(12) United States Patent
Bostley et al.

(10) Patent No.: US 11,771,383 B1
(45) Date of Patent: Oct. 3, 2023

(54) LINKAGE SYSTEM

(71) Applicant: RCI Operating Co., LLC, Hilton, NY (US)

(72) Inventors: Eric Boone Bostley, Hilton, NY (US); Brian Ernest Giardino, North Chili, NY (US)

(73) Assignee: RCI Operating Co., LLC, Hilton, NY (US)

( * ) Notice: Subject to any disclaimer, the term of this patent is extended or adjusted under 35 U.S.C. 154(b) by 0 days.

(21) Appl. No.: 18/212,766

(22) Filed: Jun. 22, 2023

(51) Int. Cl.
*A61B 6/00* (2006.01)
*A61B 6/04* (2006.01)

(52) U.S. Cl.
CPC .................. *A61B 6/0407* (2013.01)

(58) Field of Classification Search
CPC .................................................. A61B 6/0407
See application file for complete search history.

(56) References Cited

U.S. PATENT DOCUMENTS 7,527,428 B2 *  5/2009  Riley .................. A61B 6/04
5/601

* cited by examiner

*Primary Examiner* — Dani Fox
(74) *Attorney, Agent, or Firm* — Jong Patent Firm; Cheng Ning Jong; Tracy P. Jong

(57) ABSTRACT

A radiology X-ray step platform for facilitating positioning and imaging of a patient during a radiological procedure, the radiology X-ray step platform including a base structure; at least one step surface configured to support the patient during the radiological procedure, the at least one step surface is supported on the base structure; and a mobility mechanism disposed on the base structure, the mobility mechanism configured to be erectable in an erected position to facilitate transport of the base structure and retractable in a retracted position to allow the base structure to be used in a stable condition.

20 Claims, 10 Drawing Sheets

LINKAGE SYSTEM

BACKGROUND OF THE INVENTION

1. The Field of the Invention

The present invention relates to a linkage system. More specifically, the present invention is directed to a mobility aid useful for supporting and facilitating the disposition of a structure it supports in a mobile state and a static state.

2. Background Art

U.S. Pat. No. 7,527,428 to Riley (hereinafter Riley) discloses a two-step platform for radiological examination (hereinafter X-rays) of a patient's foot and ankle. X-rays can be taken of a patient's foot and ankle as the patient sits and the equipment is positioned near the foot. However, such X-ray films show a foot or ankle without bearing a load, or weight. Those X-ray films show the bony structure in the absence of stress thus limiting the appearance of cracks in the bony structure. As feet and ankles move and support a person's weight throughout the day and during exertion, X-rays of feet and ankles when under stress provide a more accurate view of the condition of the feet and ankles. Feet and ankles X-rayed while under stress may reveal cracks in the bony structure closed when the feet and ankles are not stressed. Operators of X-ray equipment and doctors have sought devices to assist in X-raying feet and ankles while supporting weight. Riley's platform raises the patient to align with the X-ray emitter and allows imaging while weight bearing. The platform has a transparent surface beneath which is provided a space to insert a plate with an X-ray film to allow an image of the foot from the vertical direction, as well as a slot to support an X-ray plate in a vertical position to image an ankle from the side. The platform provides space for both feet insuring the foot to be imaged is in its natural position, and the posture of the patient is not out of alignment. Riley's platform allows imaging from above and from the side when the foot supports a person's weight. At least three casters are provided at the rear of the platform to allow the technician to roll the platform once the handle on the front of the platform is grasped, and the platform is lifted and tipped up to place the casters in contact with the floor. The weight of the platform may make lifting and tipping it a challenge for the technician.

Although Riley demonstrated a step platform for radiological imaging of weight bearing feet and ankles, there remains a need for a step platform with a mobility mechanism that allows the step platform to be easily moved without lifting and tilting, while allowing the platform to be disposed in a stable condition when in use and being mobile when it needs to be transported.

SUMMARY OF THE INVENTION

In accordance with the present invention, there is provided a radiology X-ray step platform for facilitating positioning and imaging of a patient during a radiological procedure, the radiology X-ray step platform including:
  (a) a base structure;
  (b) at least one step surface configured to support the patient during the radiological procedure, the at least one step surface is supported on the base structure; and
  (c) a mobility mechanism disposed on the base structure, the mobility mechanism configured to be erectable in an erected position to facilitate transport of the base structure and retractable in a retracted position to allow the base structure to be used in a stable condition.

In one embodiment, the mobility mechanism is configured to transition from the erected position to the retracted position when a force is applied to the at least one step surface.

In accordance with the present invention, there is further provided a linkage system including:
  (a) an elongated member including a first end, a rotational joint, a first pivot point, a second pivot point and a second end, wherein each of the rotational joint, the first pivot point and the second pivot point of the elongated member is disposed along a lengthwise direction of the elongated member and the first pivot point is disposed at a location along the lengthwise direction of the elongated member between the rotational joint and the second pivot point and each of the rotational joint, the first pivot point and the second pivot point is disposed between the first end and the second end of the elongated member, wherein the elongated member is rotationally secured to a structure at the rotational joint of the elongated member;
  (b) a frame member including a first pivot point, a second pivot point and a rotational joint, wherein the frame member is rotationally secured to the structure at the rotational joint of the frame member;
  (c) a truss including a pair of ends; and
  (d) a variable length rod member,
wherein the variable length rod member is configured to pivotably connect the elongated member at the first pivot point of the elongated member and the frame member at the second pivot point of the frame member, one end of the truss is configured to be pivotably connected to the second pivot point of the elongated member and the other end of the truss is configured to be pivotably connected to the first pivot point of the frame member, a rotation of the frame member disposes the linkage system in a retracted position and a counter-rotation of the frame member disposes the linkage system in an erected position.

In one embodiment, the structure is a step platform. In one embodiment, the linkage system further includes at least one first wheel connected to the elongated member. In one embodiment, the at least one first wheel is a caster. In one embodiment, the linkage system further includes at least one second wheel connected to the frame member. In one embodiment, the linkage system further includes a crossbar including a pair of ends, the crossbar configured to be attached to the rotational joint of the frame member. In one embodiment, the linkage system further includes a pair of wheels each disposed on one of the pair of ends of the crossbar. In one embodiment, the pair of wheels includes a pair of casters. In one embodiment, the variable length rod member is a compression spring. In one embodiment the compression spring is a gas cylinder. In one embodiment, the linkage system further includes a foot lever connected to the crossbar to facilitate an application of a rotation of the crossbar.

An object of the present invention is to provide a radiology X-ray step platform for facilitating positioning and imaging of a patient during a radiological procedure.

Another object of the present invention is to provide a step platform with a mobility mechanism that allows the step platform to be easily moved without lifting and tilting, while allowing the platform to be disposed in a stable platform when in use and being mobile when it needs to be transported.

Another object of the present invention is to provide a radiology X-ray step platform which can transform automatically into an immobile and stable platform when a patient steps on the platform that is disposed in a state suitable for mobility.

Another object of the present invention is to provide a radiology X-ray step platform for facilitating positioning and imaging of a patient during a radiological procedure that is easily transportable by the user without lifting and/or tipping the platform in order to eliminate the risk of back injury.

Another object of the present invention is to provide a radiology X-ray step platform for facilitating positioning and imaging of a patient during a radiological procedure that raises the foot or ankle to align with the X-ray transmitter.

Another object of the present invention is to provide a radiology X-ray step platform for facilitating positioning and imaging of a patient during a radiological procedure where X-ray images can be taken laterally from the front, back or side of the patient's ankle, and top of the patient's foot.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

PARTS LIST

2—linkage system
4—elongated member
6—first end of elongated member
8—rotational joint of elongated member
10—first pivot point of elongated member
12—second pivot point of elongated member
14—second end of elongated member
16—frame member
18—rotational joint of frame member
20—first pivot point of frame member
22—second pivot point of frame member
24—floor
26—truss
28—wheel, e.g., caster
30—rod member, e.g., gas spring
32—wheel, e.g., caster
34—wheel, e.g., caster
36—foot lever
38—foot
40—step
42—step
44—slot
46—railing
48—step platform
50—back of platform
52—direction
54—direction
56—base structure
58—crossbar
60—direction in which platform is tilted
62—direction in which platform is stepped on
64—crossbar

PARTICULAR ADVANTAGES OF THE INVENTION

The present linkage system allows easy deployment and retraction of caster wheels or casters, making the transition from a mobile posture or position to a stationary posture or position or from a stationary posture to a mobile posture of the structure the linkage system supports effortless. A simple act of tilting a present platform in a stationary posture back allows the compression spring to actuate to put the platform in an erected mobile posture. The platform may alternatively be disposed in a mobile posture by stepping on a foot lever in a first direction. The platform may be made stable, i.e., changed from its mobile-capable position to its stable position by simply stepping on the lower of the two steps of the platform. The platform may alternatively be disposed in a stable position by stepping on the foot lever in a second direction opposite the first direction.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Figure 1:
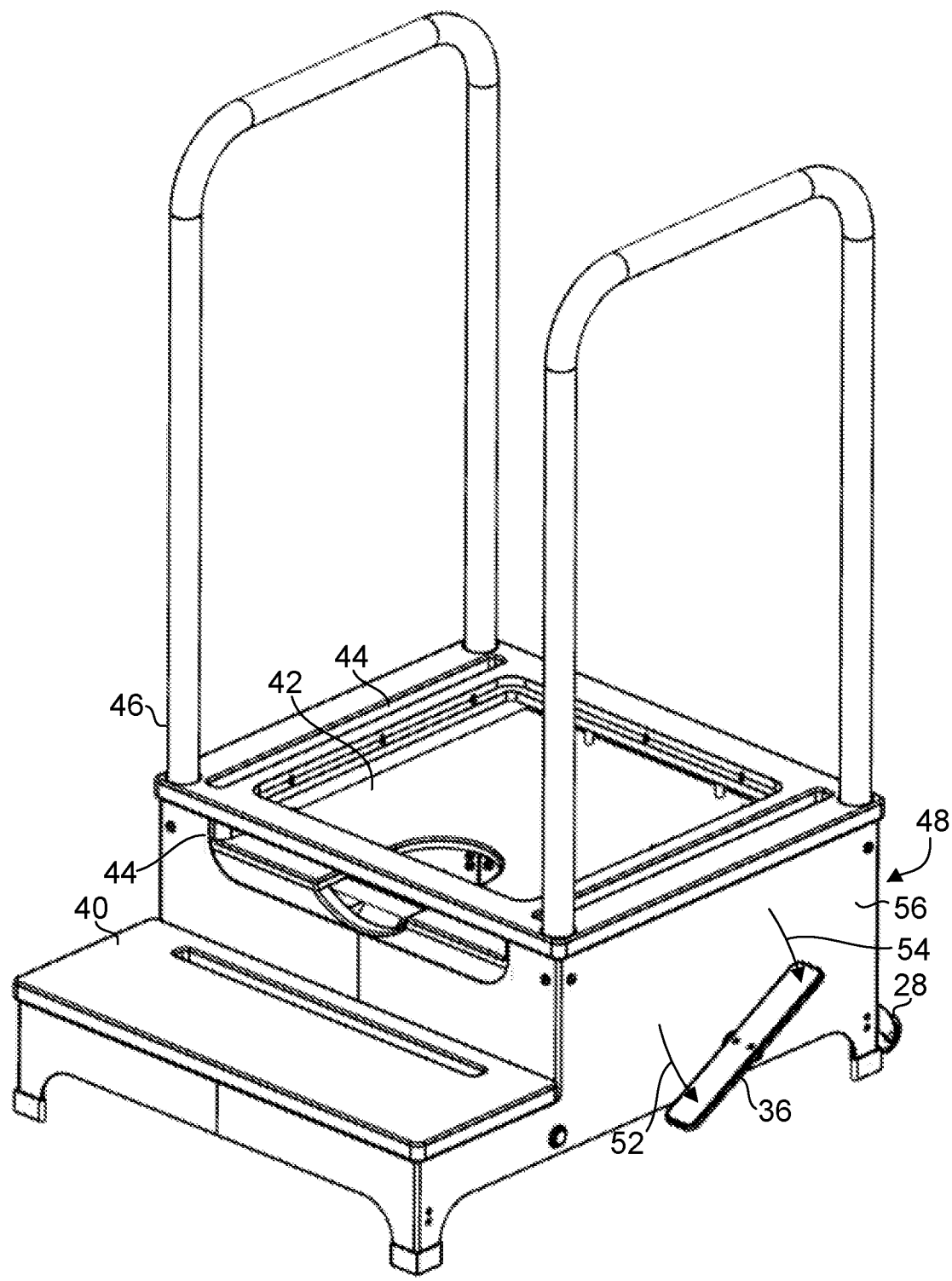
FIG. 1 is a top front perspective view of a radiology X-ray step platform for facilitating positioning and imaging of a patient during a radiological procedure.

FIG. 1 is a top front perspective view of a radiology X-ray step platform 48 for facilitating positioning and imaging of a patient during an X-ray procedure. The radiology X-ray step platform 48 includes a base structure 56, step surfaces 40, 42 supported on the is base structure 56 to support a patient during an X-ray procedure and a mobility mechanism disposed within the base structure 56. The mobility mechanism can be easily put into a mobile mode or a stable immobile mode by stepping on a foot lever 36 of the platform 48. For instance, the foot lever 36 can be stepped in direction 52 to dispose the linkage system shown elsewhere herein in a retracted position or the platform in a stable position. The foot lever 36 can be stepped in direction 54 to dispose the linkage system shown elsewhere herein in an extended or erected position to dispose the platform in a mobile-ready position. The mobility mechanism, when disposed in the mobile mode, allows a technician or user to effortlessly move the platform to the X-ray room from a storage room for an X-ray procedure to be done. In use, a patient steps on the first step 40 and climbs up to the second step 42 while holding onto the railing 46, after the technician puts the mobility mechanism in the stable immobile mode or after the patient steps on the first step 40 as the simple act of stepping on the first step 40 automatically causes the mobility mechanism and hence the platform 48 to be disposed in a stable immobile mode. Using the platform, the patient's foot and ankle can be positioned at the correct height to be aligned with the X-ray transmitter and allows X-rays to be taken when the foot or ankle is weight bearing. The second higher step 42 is a transparent glass surface below which is a horizontal slot 44 for insertion of an X-ray plate. This allows X-rays to be taken from above the patient's feet. Two vertical slots 44 are useful for holding vertical X-ray plates and permitting X-rays to be taken of the patient's ankles from both sides. It is important that the platform be completely immobile prior to the patient stepping on the first step 40 in order to ensure that the patient does not lose his or her balance and fall. If the platform not already disposed in an immobile position, the platform can transition into its immobile position simply by receiving a force placed on the first step 40, e.g., when a patient steps on the first step 40. The inventive concept of the present X-ray step platform lies not in the shape or construction of the base structure of the platform, but rather in the ease with which the user can move the platform from a storage area to the X-ray transmitter without lifting the front end of the platform and tilting it in order to place casters or wheels on the back of the platform in contact with the floor, as Riley's platform requires. The Riley platform may be rather heavy and difficult for some technicians to lift, risking a back injury and the present invention with the mobility mechanism eliminates this risk.

Figure 2:
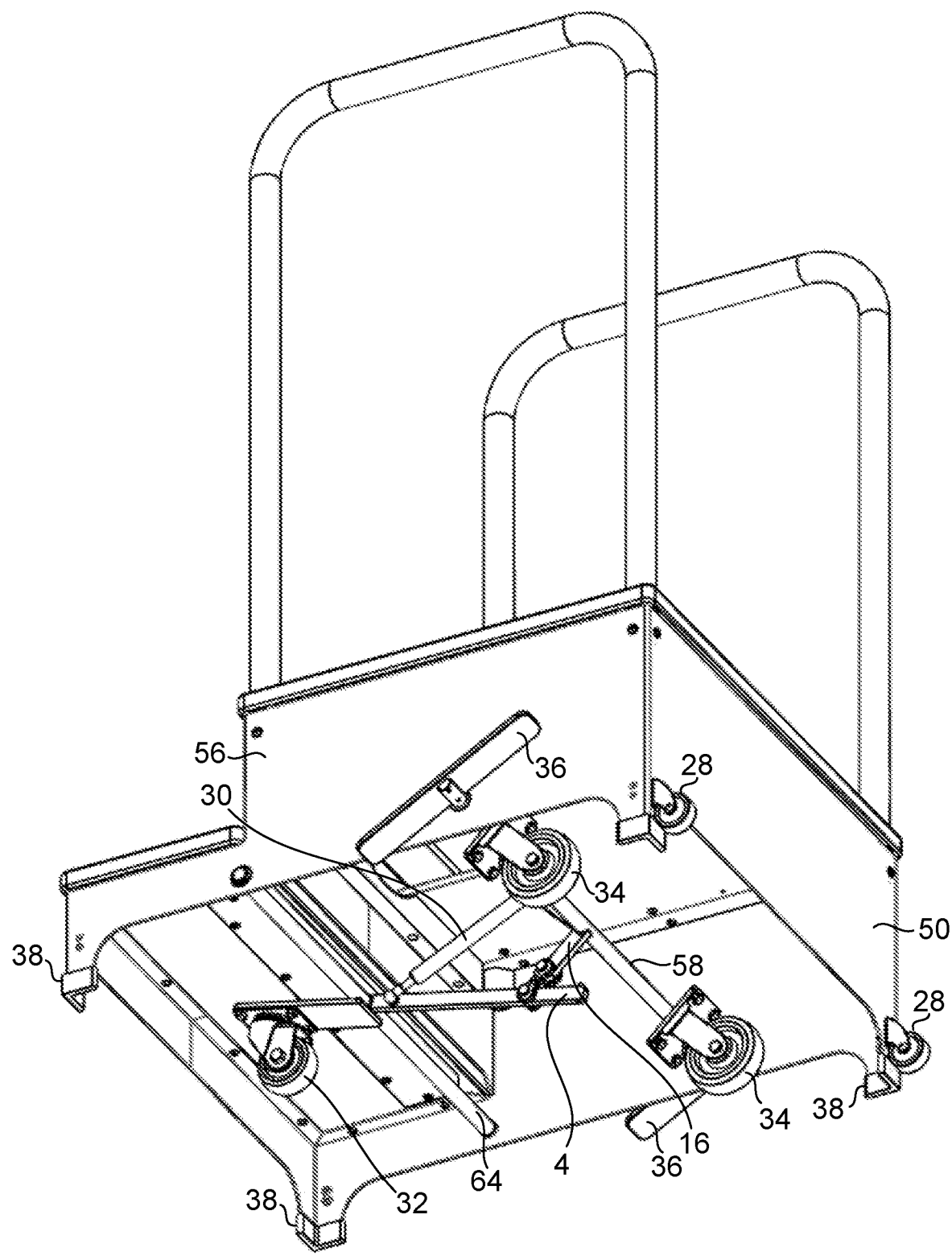
FIG. 2 is a bottom rear perspective view of a radiology X-ray step platform for facilitating positioning and imaging of a patient during a radiological procedure where its linkage system is disposed in a retracted position.
Figure 3:
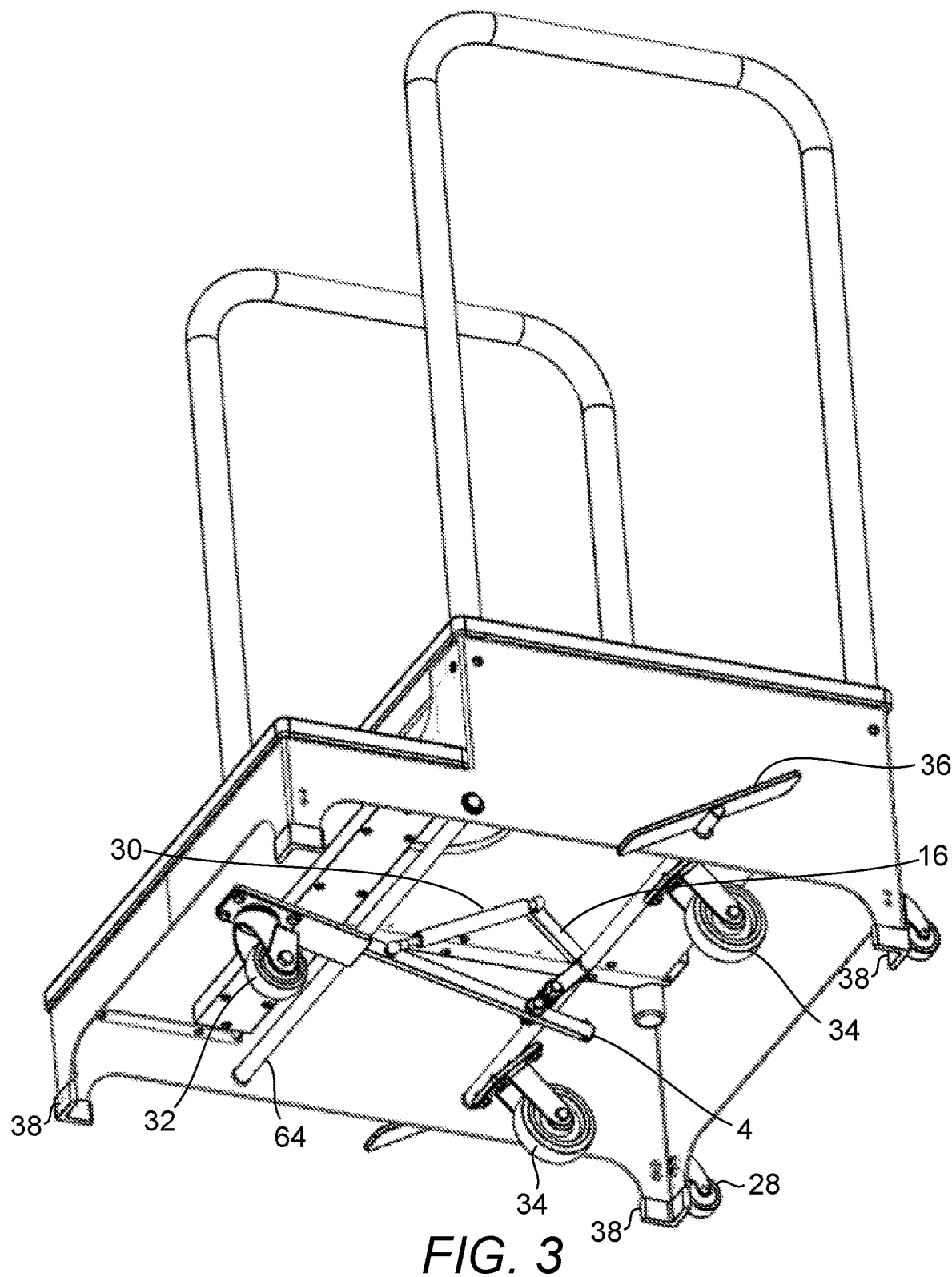
FIG. 3 is a bottom front perspective view of the linkage system in a retracted position.
Figure 4:
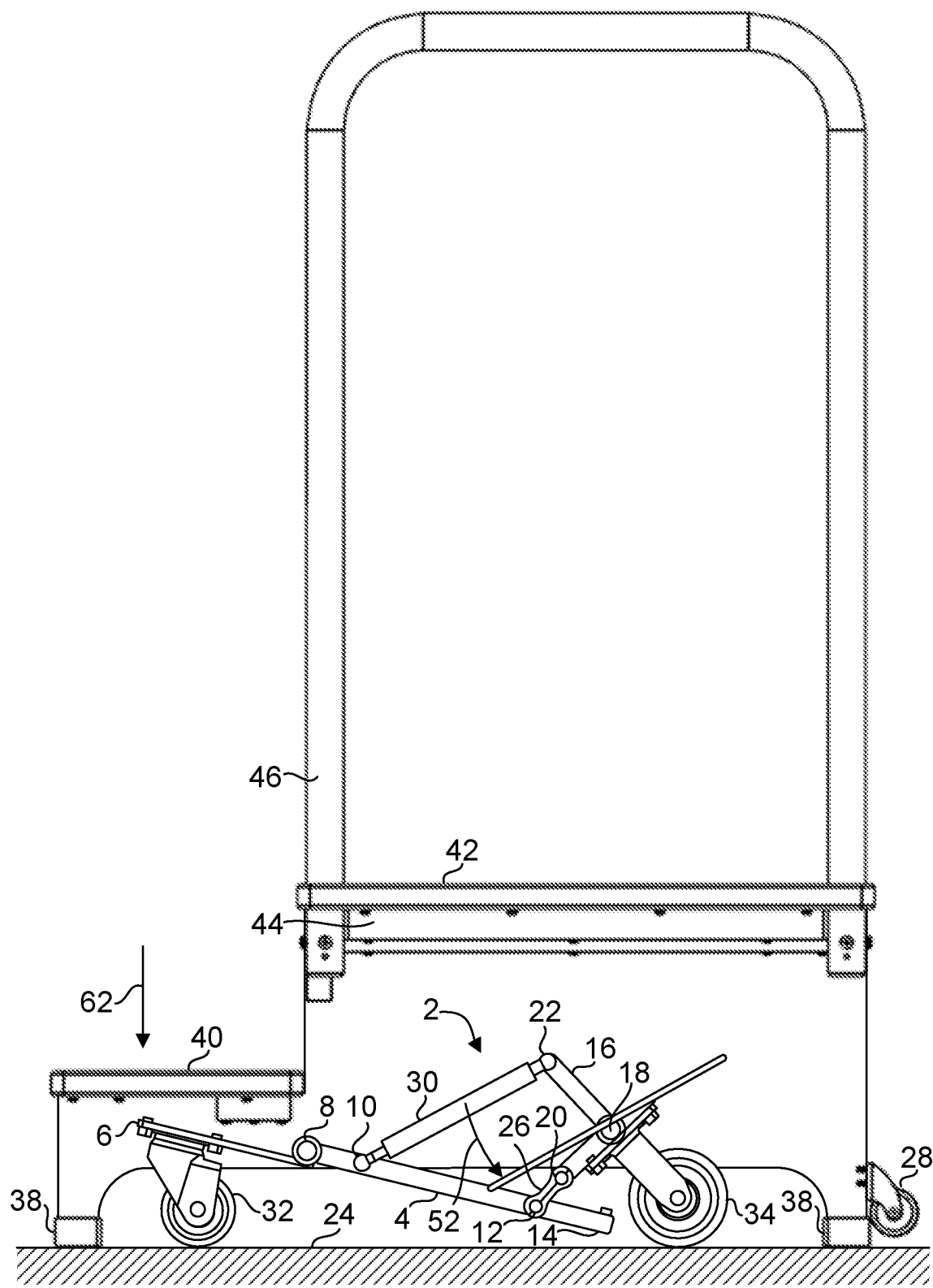
FIG. 4 is a side view of a radiology X-ray step platform for facilitating positioning and imaging of a patient during a radiological procedure where its linkage system is disposed in a retracted position.
Figure 5:
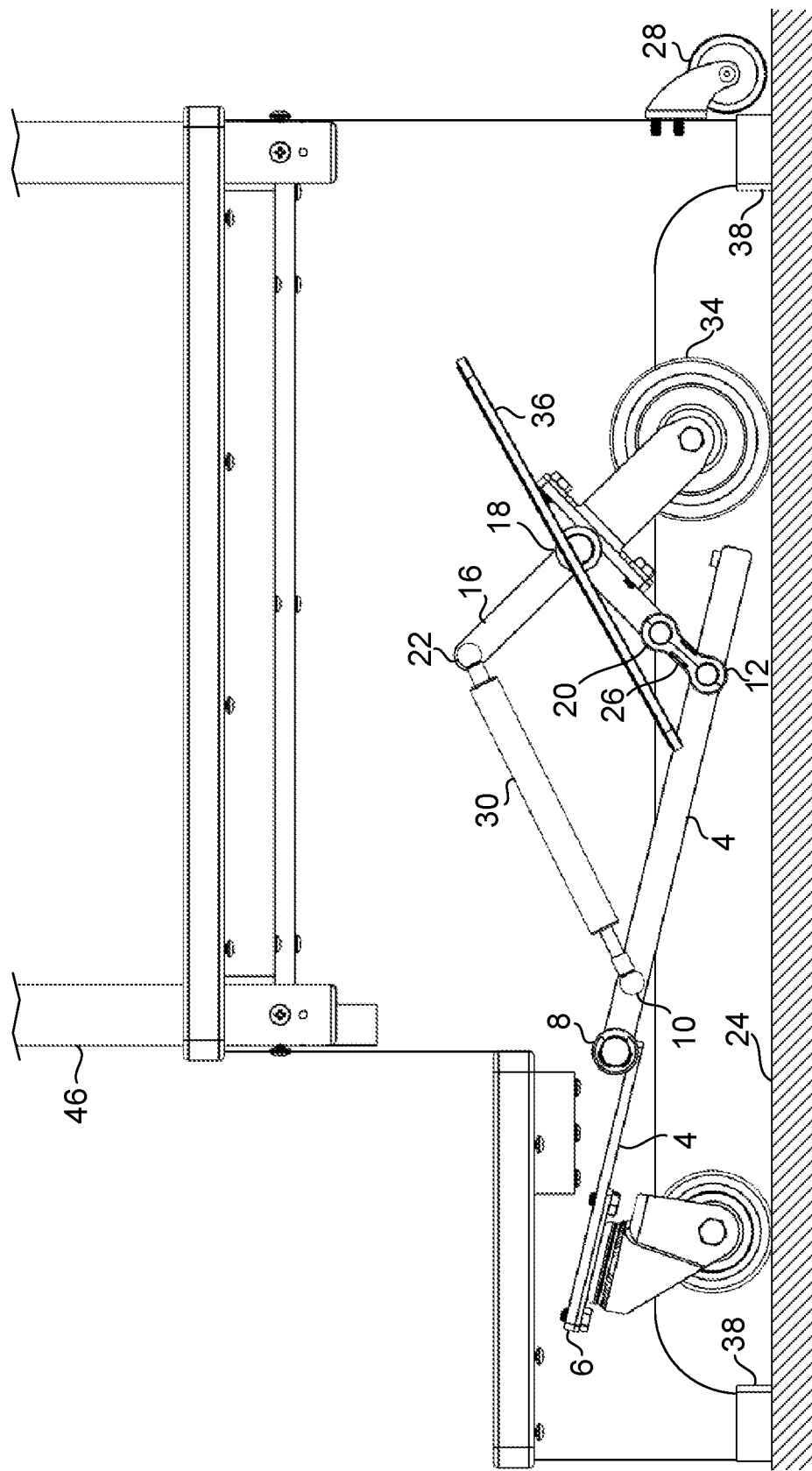
FIG. 5 is a detailed side view of the linkage system of the mobility mechanism of FIG. 4.

FIG. 2 is a bottom rear perspective view of a radiology X-ray step platform for facilitating positioning and imaging of a patient during a radiological procedure where its linkage system 2 is disposed in a retracted position. FIG. 3 is a bottom front perspective view of the linkage system 2 in a retracted position. FIG. 4 is a side view of a radiology X-ray step platform for facilitating positioning and imaging of a patient during a radiological procedure where its linkage system 2 is disposed in a retracted position. FIG. 5 is a detailed side view of the linkage system 2 of the mobility mechanism of FIG. 4. In FIGS. 4-5, a side plate of the platform 48 has been removed to reveal the details of the linkage system 2 disposed in the interior space of the base structure 56. The radiology X-ray step platform essentially includes a base structure 56, at least one step surface, e.g., two step surfaces 40, 42 configured to support the patient during the radiological procedure and a mobility mechanism disposed on the base structure 56. The mobility mechanism is configured to be erectable in an erected position to facilitate transport of the base structure 56 and retractable in a retracted position to allow the base structure 56 to be used in a stable condition. The step surfaces 40, 42 are supported on the base structure 56. The mobility mechanism includes a linkage system 2 having wheels or casters 32, 34 which allow the mobility mechanism to be disposed in an erected or extended state to make the platform rollable on a floor and a retracted state to make the platform not rollable on a floor and therefore stable with respect to the floor 24. The linkage system 2 includes an elongated member 4, a frame member 16, a truss 26 and a variable length rod member 30. The elongated member 4 includes a first end 6, a rotational joint 8, a first pivot point 10, a second pivot point 12 and a second end 14. Each of the rotational joint 8, the first pivot point 10 and the second pivot point 12 of the elongated member 4 is disposed along a lengthwise direction of the elongated member 4 and the first pivot point 10 is disposed at a location along the lengthwise direction of the elongated member 4 between the rotational joint 8 and the second pivot point 12. Each of the rotational joint 8, the first pivot point 10 and the second pivot point 12 is disposed between the first end 6 and the second end 14 of the elongated member 4. The elongated member 4 is rotationally secured to the base structure 56 at rotational joint 8. The frame member 16 includes the first pivot point 20, the second pivot point 22 and the rotational joint 18. The frame member 16 is rotationally secured to the base structure 56 at rotational joint 18. The truss 26 includes a pair of ends. One end of the truss 26 is configured to be pivotably connected to the second pivot point 12 of the elongated member 4 and the other end of the truss is configured to be pivotably connected to the first pivot point 20 of the frame member 16. One end of the variable length rod member 30 is pivotably connected to the elongated member 4 at the first pivot point 10 of the elongated member 4 while the other end of the variable length rod member 30 is pivotably connected to the second pivot point 22 of the frame member 16. The frame member 16 is pivotably connected to the truss 26 at the first pivot point 20 of the frame member 16. The other end of truss 26 is pivotably connected to the elongated member 4 the second pivot point 12 of the elongated member 4. A rotation of the frame member 16 disposes the linkage system 2 in a retracted position and a counter-rotation of the frame member 16 disposes the linkage system in an erected position. The base structure 56 is essentially a step platform, e.g., the two-step platform shown throughout. The linkage system 2 further includes a first wheel 32 connected to the elongated member 4. In one embodiment, the first wheel 32 is a swivel caster that allows the platform 48 to roll more easily in all directions. Any additional number of wheels or casters may provide a wider and more stable mobility base albeit unnecessarily. The linkage system 2 further includes two second wheels 34 connected to the frame member 16. The linkage system 2 further includes a crossbar 58 including a pair of ends. The crossbar 58 is configured to be rigidly attached to the rotational joint 18 of the frame member 16. The pair of wheels 34 are each disposed on one of the pair of ends of the crossbar 58 to provide a larger and stable mobility base on the rear end of the platform 48. Two wheels 34 are used in the rear end of the platform 48 although one would have sufficed if the front end of the platform 48 had been equipped with at least two wheels. There is further provided a second crossbar 64 including a pair of ends. Here, the crossbar 64 is configured to be rigidly attached to the rotational joint 8 of the elongated member 4. In one embodiment, the pair of wheels includes a pair of casters. In one embodiment, the variable length rod member is a compression spring. In one embodiment, the compression spring is a gas spring which provides a more compact variable length rod member 30 while meeting the load requirements that allow the linkage system 2 to be disposed in its erected or retracted state compared to a mechanical spring. The linkage system includes at least a wheel or caster disposed on the first end of the elongated member 4 to ensure that the rollable base is sufficiently large to stably support the base structure 56. Wheels 28 are provided at two corners of the back 50 of the platform 48, with their mounting location each about a few inches from the base of a foot 38. A technician has an option of using another mode to move the platform 48 if he or she so chooses by tilting back the platform such that the platform 48 is supported mostly on these wheels 28 while the technician guides the platform 48 by holding onto the railings 46.

Referring to FIGS. 2-5, it shall be noted that the wheel disposed on the front of the linkage system 2, i.e., wheel 32, as well as the two wheels on the rear of the linkage system 2, i.e., wheels 34, are raised. The linkage system further includes two foot levers 36, each connected to one end of the crossbar 58 to facilitate an application of a rotation of the crossbar 58. Although the wheels 32, 34 appear to be contacting the floor 24 even while disposed in the retracted position, the wheels 32, 34 and hence the linkage system 2 are configured to be disposed in a manner insufficiently loaded, e.g., in the compression, e.g., gas, spring 30, to lift the platform 48 and hence to cause the feet 38 to be lifted off the floor 38, therefore allowing the platform 48 to remain stable or immobile, e.g., due to sufficient friction between the feet 38 and the floor 24 even while the platform 48 is being pushed from a side, eliminating the risk of the patient losing his or her balance and falling. The platform 48 remains in this retracted position when the patient steps off the platform 48. The suitable gas spring 30 shall be carefully selected to provide one with a suitable load or pressure rating so as not to cause the platform to be inadvertently lifted once the linkage system 2 has been disposed in a retracted position. There are two modes to dispose the linkage system 2 in this position. In one mode, if the linkage system 2 is not already disposed in its retracted position, e.g., a position shown in FIG. 8, the linkage system 2 can be disposed in its retracted position by stepping on the front of the foot lever 36, i.e., in direction 52 as shown in FIG. 4, essentially rotating the frame member 16 counter-clockwise about the rotational joint 18 of the frame member 16 and rotating elongated member 4 clockwise about its rotational joint 8 and compressing the gas spring 30. Both rotational joints 18 and 8 are supported, e.g., indirectly via crossbar 58 and crossbar 64, respectively by the base structure 56, via, e.g., radial ball bearing joints or bushings disposed in the side plates of the base structure 56, but capable to rotate with respect to the bushings. In a second mode, the linkage system 2 can be disposed in its retracted position by stepping on surface 40 in direction 62, the technician or the patient's weight alone, e.g., over about 100 lbs, would be sufficient to dispose the linkage system 2 in the retracted position which would cause the components of the linkage system 2 to traverse similar motions disclosed elsewhere herein to finally assume its retracted position, disposing the platform in a stable position for use by a patient. It shall be noted then that the present linkage system 2 automatically disposes the platform 48 in a safe operating condition even if a patient accidentally steps on a platform which is still capable of mobility.

Figure 6:
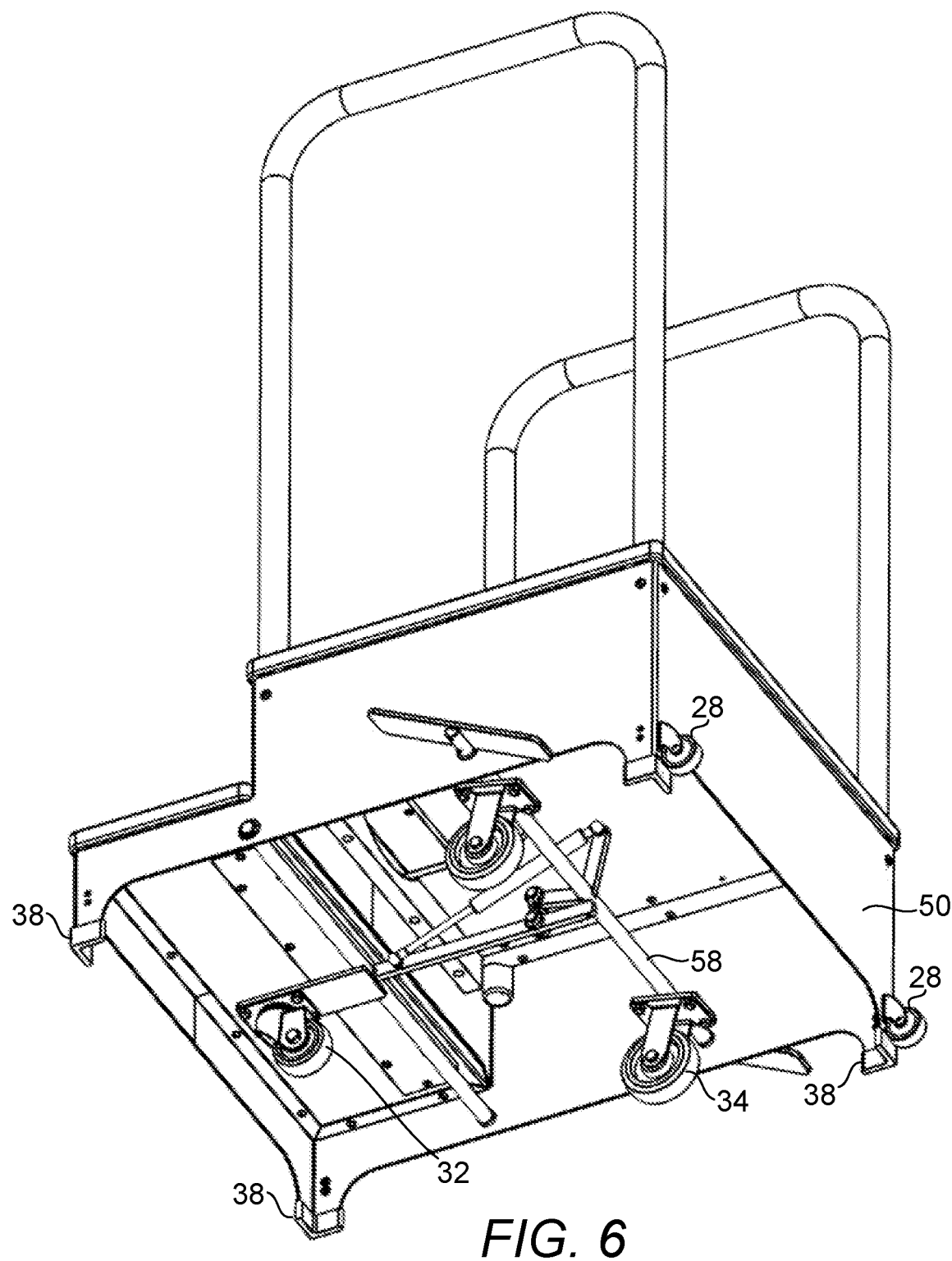
FIG. 6 is a bottom rear perspective view a radiology X-ray step platform for facilitating is positioning and imaging of a patient during a radiological procedure where its linkage system is disposed in an erected position.
Figure 7:
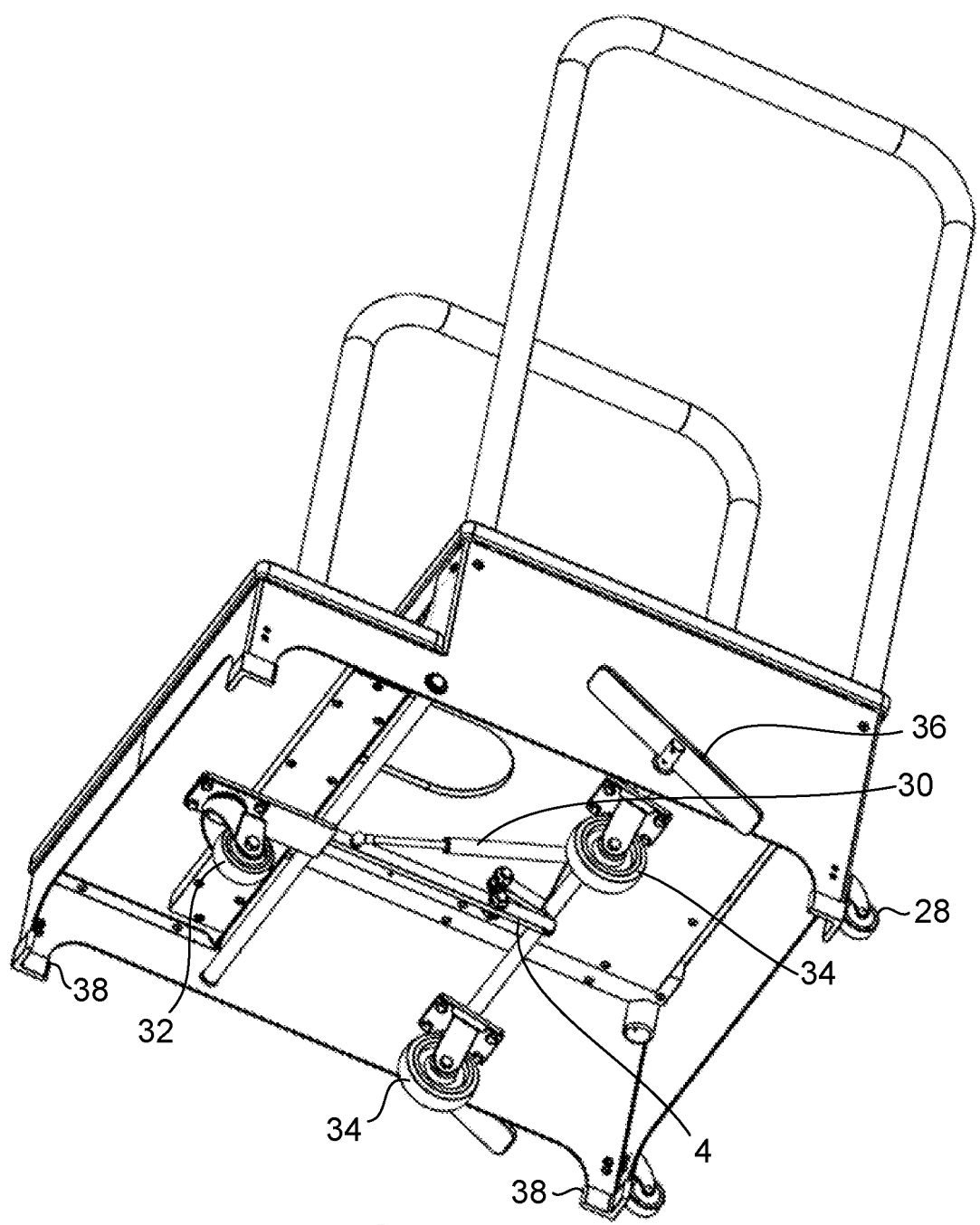
FIG. 7 is a bottom front perspective view of the linkage system in an erected position.
Figure 8:
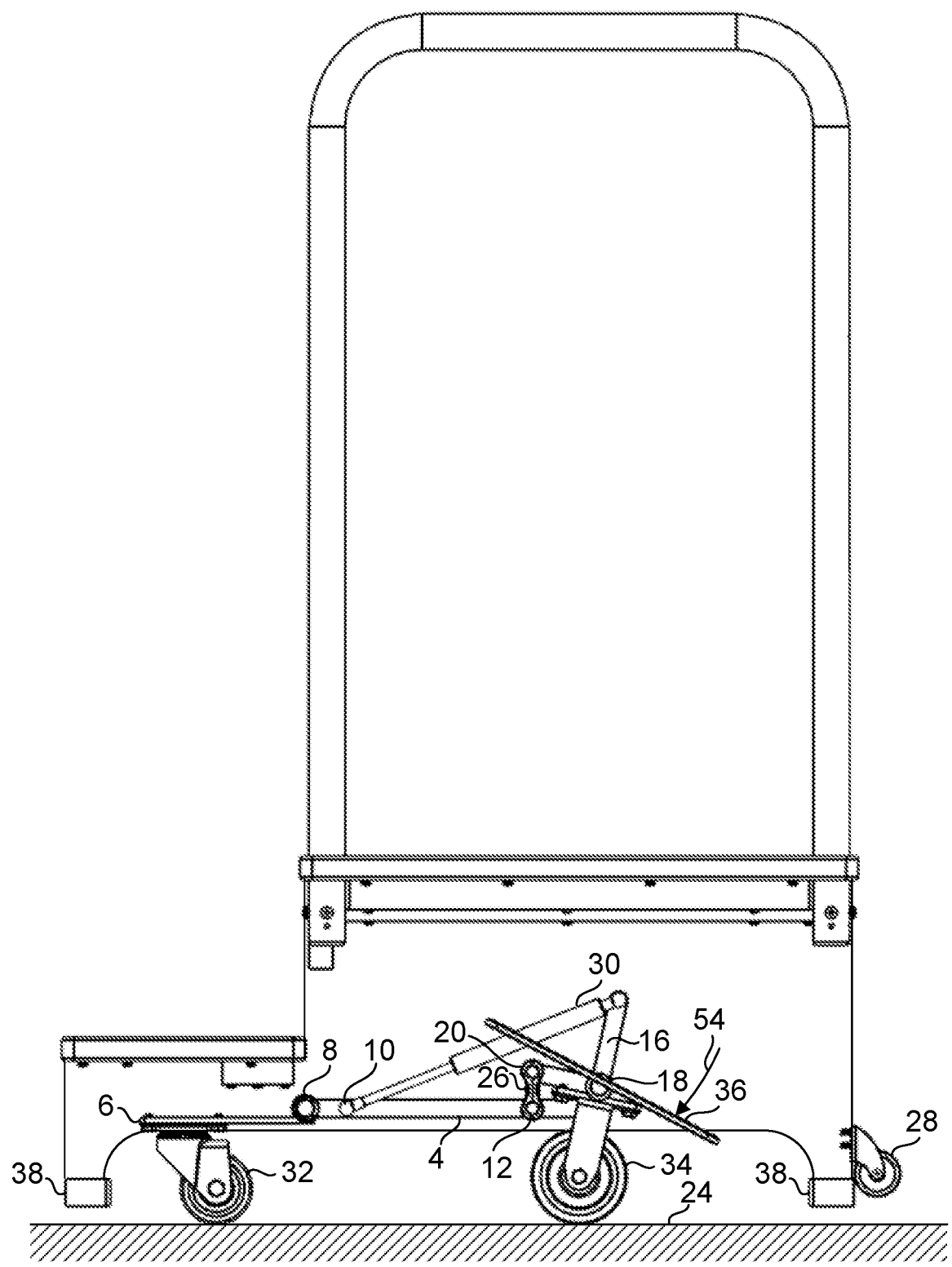
FIG. 8 is a side view of a radiology X-ray step platform for facilitating positioning and imaging of a patient during a radiological procedure where its linkage system is disposed in an erected position.
Figure 9:
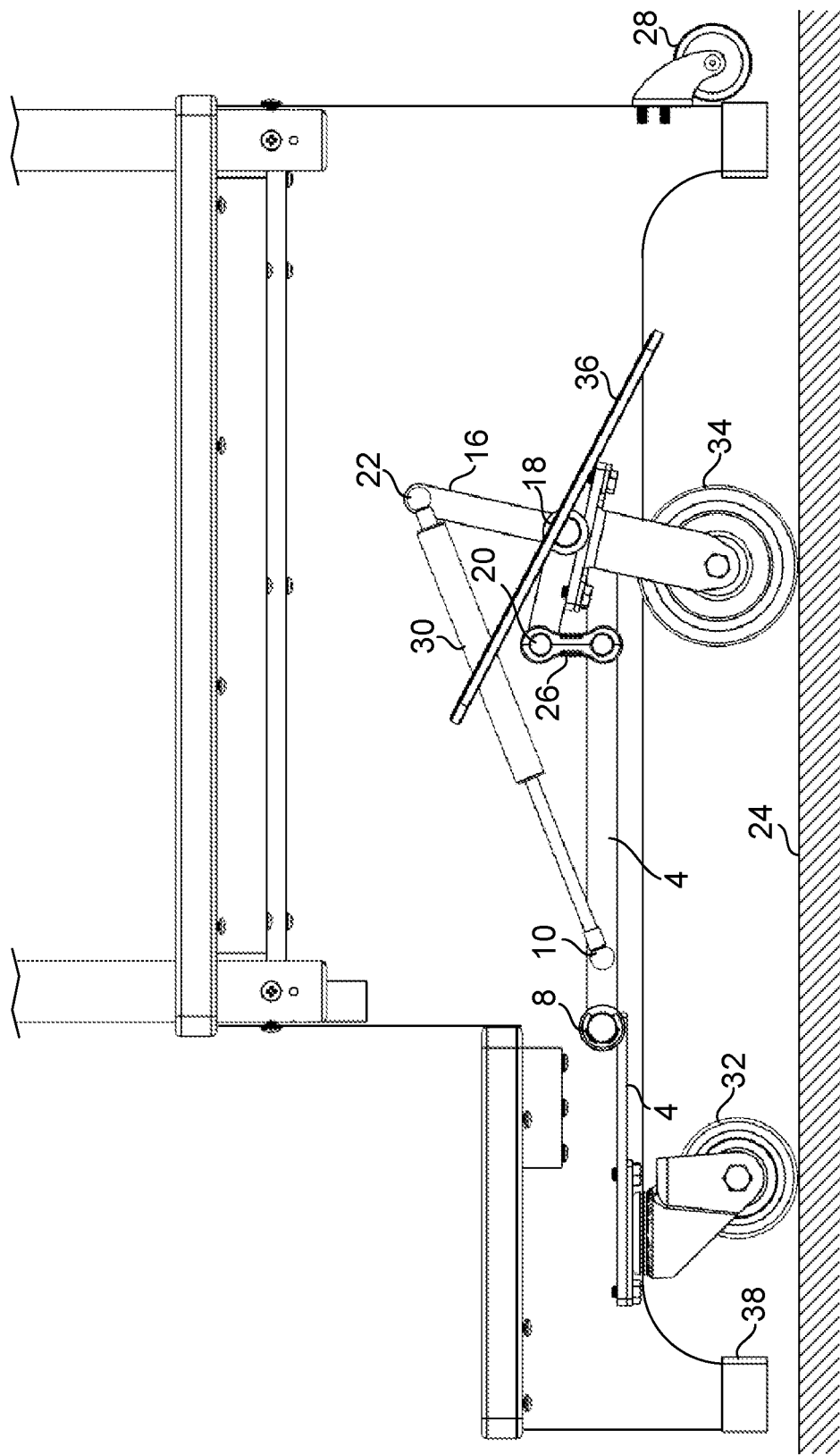
FIG. 9 is a detailed side view of the linkage system of the mobility mechanism of FIG. 8.

FIG. 6 is a bottom rear perspective view a radiology X-ray step platform 48 for facilitating positioning and imaging of a patient during a radiological procedure where its linkage system is disposed in an erected position. FIG. 7 is a bottom front perspective view of the linkage system in an erected position. FIG. 8 is a side view of a radiology X-ray step platform for facilitating positioning and imaging of a patient during a radiological procedure where its linkage system is disposed in an erected position. FIG. 9 is a detailed side view of the linkage system of the mobility mechanism of FIG. 8. In FIGS. 8-9, again, a side plate of the platform 48 has been removed to reveal the details of the linkage system 2 disposed in the interior space of the base structure 56. Referring to FIGS. 6-9, it shall be noted that the wheel disposed on the front of the linkage system 2, i.e., wheel 32, as well as the two wheels on the rear of the linkage system 2, i.e., wheels 34, are lowered, raising the platform 48 such that the feet 38 no longer stay in contact with the floor 24. There are two modes to dispose the linkage system 2 in this position. In one mode, if the linkage system 2 is not already disposed in its erected position, e.g., a position shown in FIG. 4, the linkage system 2 can be disposed in its retracted position by stepping on the rear of the foot lever 36, i.e., in direction 54 as shown in FIG. 8, essentially rotating the frame member 16 clockwise about the rotational joint 18 of the frame member 16 and rotating elongated member 4 counter-clockwise about its rotational joint 8 and relieving the gas spring 30. In a second mode, the linkage system 2 can be disposed in its erected position by following the procedure as shown in FIG. 10.

Figure 10:
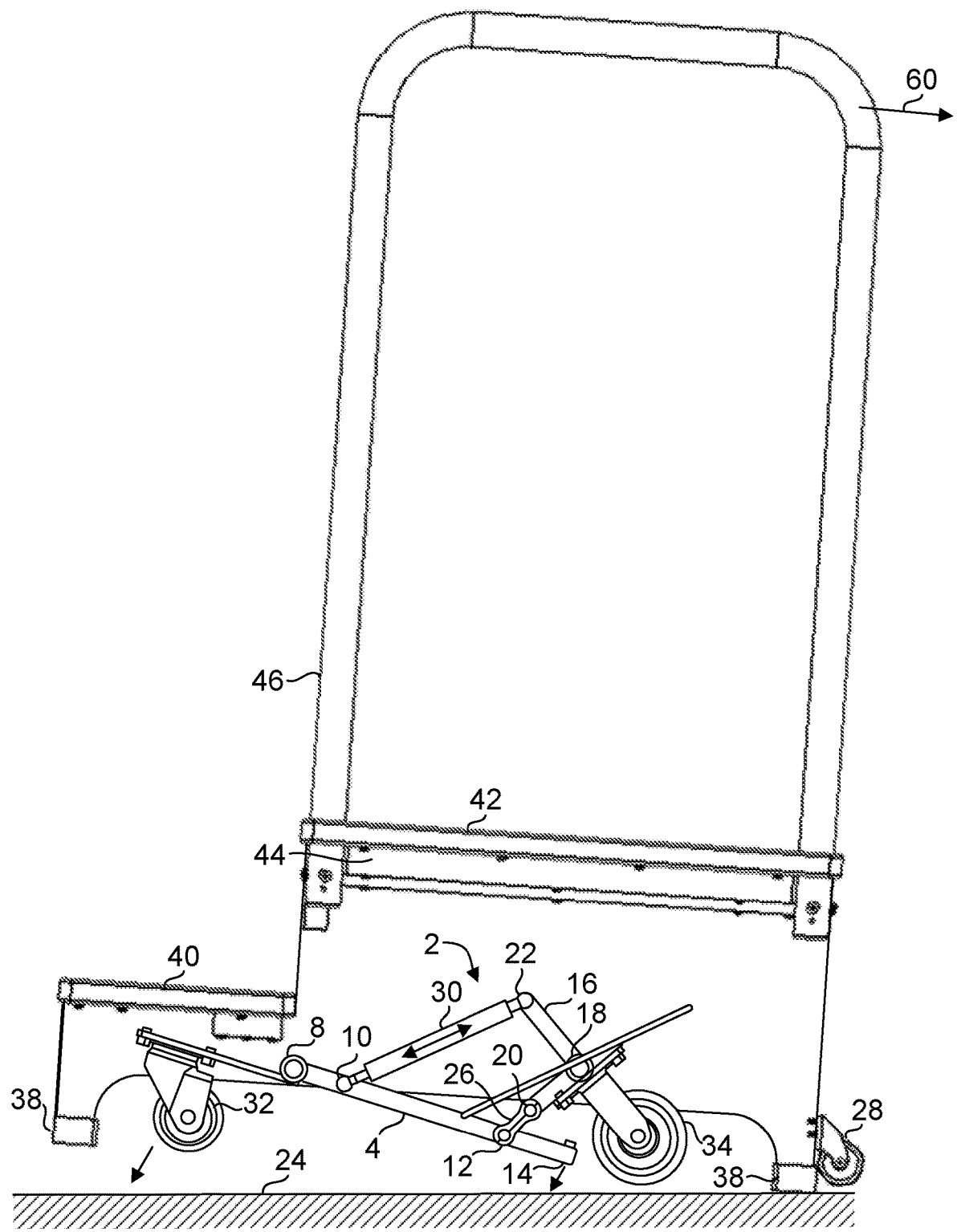
FIG. 10 is a side view of a radiology X-ray step platform for facilitating positioning and imaging of a patient during a radiological procedure where the platform is shown being tilted backwards on the rear wheels to put the wheels in an erected position after initially being disposed in a stable condition.

FIG. 10 is a side view of the linkage system 2 when a stable platform as shown in FIG. 4 is tilted backwards in direction 60 on the rear feet 38. Again, a side wall of the platform has been removed to reveal the linkage system disposed therein. This action allows the gas spring 30 to extend, allowing the frame member 16 to rotate clockwise. This allows wheels 32 and 34 to move downwardly until the linkage system becomes fully erected to eventually assume a position shown in FIGS. 8-9. Upon allowing the compressed gas spring 30 to extend by relieving the front end constraint on the platform caused by the weight of the platform and the floor 24, the linkage system 2 rearranges itself due to the potential energy stored in the gas spring 30 to return to the linkage system 2 to its mobile condition or position.

The detailed description refers to the accompanying drawings that show, by way of illustration, specific aspects and embodiments in which the present disclosed embodiments may be practiced. These embodiments are described in sufficient detail to enable those skilled in the art to practice aspects of the present invention. Other embodiments may be utilized, and changes may be made without departing from the scope of the disclosed embodiments. The various embodiments can be combined with one or more other embodiments to form new embodiments. The detailed description is, therefore, not to be taken in a limiting sense, and the scope of the present invention is defined only by the appended claims, with the full scope of equivalents to which they may be entitled. It will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosed embodiments includes any other applications in which embodiments of the above structures and fabrication methods are used. The scope of the embodiments should be determined with reference to the appended claims, along with the full scope of equivalents to which such claims are entitled.

What is claimed herein is:

1. A radiology X-ray step platform for facilitating positioning and imaging of a patient during a radiological procedure, said radiology X-ray step platform comprising:
    (a) a base structure;
    (b) at least one step surface configured to support the patient during the radiological procedure, said at least one step surface is supported on said base structure; and
    (c) a mobility mechanism disposed on said base structure, said mobility mechanism configured to be erectable in an erected position to facilitate transport of said base structure and retractable in a retracted position to allow said base structure to be used in a stable condition.

2. The radiology X-ray step platform of claim 1, wherein said mobility mechanism is configured to transition from said erected position to said retracted position when a force is applied to said at least one step surface.

3. A linkage system comprising:
    (a) an elongated member comprising a first end, a rotational joint, a first pivot point, a second pivot point and a second end, wherein each of said rotational joint, said first pivot point and said second pivot point of said elongated member is disposed along a lengthwise direction of said elongated member and said first pivot point is disposed at a location along said lengthwise direction of said elongated member between said rotational joint and said second pivot point and each of said rotational joint, said first pivot point and said second pivot point is disposed between said first end and said second end of said elongated member, wherein said elongated member is rotationally secured to a structure at said rotational joint of said elongated member;
    (b) a frame member comprising a first pivot point, a second pivot point and a rotational joint, wherein said frame member is rotationally secured to said structure at said rotational joint of said frame member;
    (c) a truss comprising a pair of ends; and
    (d) a variable length rod member,
wherein said variable length rod member is configured to pivotably connect said elongated member at said first pivot point of said elongated member and said frame member at said second pivot point of said frame member, one end of said truss is configured to be pivotably connected to said second pivot point of said elongated member and the other end of said truss is configured to be pivotably connected to said first pivot point of said frame member, a rotation of said frame member disposes said linkage system in a retracted position and a counter-rotation of said frame member disposes said linkage system in an erected position.

4. The linkage system of claim 3, wherein said structure is a step platform.

5. The linkage system of claim 3, further comprising at least one first wheel connected to said elongated member.

6. The linkage system of claim 5, wherein said at least one first wheel is a caster.

7. The linkage system of claim 3, further comprising at least one second wheel connected to said frame member.

8. The linkage system of claim 3, further comprising a crossbar comprising a pair of ends, said crossbar configured to be attached to said rotational joint of said frame member.

9. The linkage system of claim 8, further comprising a foot lever connected to said crossbar to facilitate an application of a rotation of said crossbar.

10. The linkage system of claim 8, further comprising a pair of wheels each disposed on one of said pair of ends of said crossbar.

11. The linkage system of claim 10, wherein said pair of wheels comprises a pair of casters.

12. The linkage system of claim 3, wherein said variable length rod member is a compression spring.

13. The linkage system of claim 12, wherein said compression spring is a gas spring.

14. A linkage system comprising:
    (a) an elongated member comprising a first end, a rotational joint, a first pivot point, a second pivot point and a second end, wherein each of said rotational joint, said first pivot point and said second pivot point of said elongated member is disposed along a lengthwise direction of said elongated member and said first pivot point is disposed at a location along said lengthwise direction of said elongated member between said rotational joint and said second pivot point and each of said rotational joint, said first pivot point and said second pivot point is disposed between said first end and said second end of said elongated member, wherein said elongated member is rotationally secured to a structure at said rotational joint of said elongated member;
    (b) a frame member comprising a first pivot point, a second pivot point and a rotational joint, wherein said frame member is rotationally secured to said structure at said rotational joint of said frame member;
    (c) a truss comprising a pair of ends; and
    (d) a compression spring,
wherein said compression spring is configured to pivotably connect said elongated member at said first pivot point of said elongated member and said frame member at said second pivot point of said frame member, one end of said truss is configured to be pivotably connected to said second pivot point of said elongated member and the other end of said truss is configured to be pivotably connected to said first pivot point of said frame member, a rotation of said frame member disposes said linkage system in a retracted position and a counter-rotation of said frame member disposes said linkage system in an erected position.

15. The linkage system of claim 14, wherein said structure is a step platform.

16. The linkage system of claim 14, wherein said compression spring is a gas spring.

17. The linkage system of claim 14, further comprising at least one first wheel connected to said elongated member.

18. The linkage system of claim 14, further comprising at least one second wheel connected to said frame member.

19. The linkage system of claim 14, further comprising a crossbar comprising a pair of ends, said crossbar configured to be attached to said rotational joint of said frame member.

20. The linkage system of claim 19, further comprising a foot lever connected to said crossbar to facilitate an application of a rotation of said crossbar.

\* \* \* \* \*